(12) United States Patent
Sümegi

(10) Patent No.: US 6,451,851 B1
(45) Date of Patent: Sep. 17, 2002

(54) PHARMACEUTICAL COMPOSITION WITH ANTIVIRAL ACTIVITY CONTAINING AN HYDROXYMIC ACID DERIVATIVE AND AN ANTIVIRAL AGENT

(75) Inventor: Balázs Sümegi, Pécs (HU)

(73) Assignee: N-Gene Research Laboratories Inc., New York, NY (US)

(*) Notice: Subject to any disclaimer, the term of this patent is extended or adjusted under 35 U.S.C. 154(b) by 0 days.

(21) Appl. No.: 09/446,650

(22) PCT Filed: Jun. 22, 1998

(86) PCT No.: PCT/IB98/00960

§ 371 (c)(1), (2), (4) Date: Mar. 23, 2000

(87) PCT Pub. No.: WO98/58675

PCT Pub. Date: Dec. 30, 1998

(30) Foreign Application Priority Data

Jun. 23, 1997 (HU) ............................................ 97 01080

(51) Int. Cl.$^7$ ...................... A61K 31/215; A61K 43/66
(52) U.S. Cl. ..................... 514/507; 514/508; 514/229.2
(58) Field of Search ................................ 514/507, 508, 514/229.2

(56) References Cited

FOREIGN PATENT DOCUMENTS

| WO | WO 97/13504 | * 4/1997 | .......... A61K/31/15 |
|---|---|---|---|
| WO | 97 13504 | 4/1999 | .......... A61K/31/15 |

OTHER PUBLICATIONS

Westarp et al, 120CA:153741, Sep. 23, 1993.*

Malley S.D. et al, Proc. Natl. Acad. Sci. U.S.A., 1994, 91/3, (11017–11021), XP000572692 USA see p. 11020, col. 1, paragraph 3.

* cited by examiner

Primary Examiner—Russell Travers
(74) Attorney, Agent, or Firm—Birch Stewart Kolasch & Birch LLP

(57) ABSTRACT

The invention refers to pharmaceutical compositions having an enhanced antiviral activity and/or decreased side effects. The composition comprises a hydroximic acid derivative of formula (I), or a therapeutically useful acid addition salt thereof and a known antiviral agent or, if desired, a therapeutically useful acid addition or therapeutically useful salt thereof.

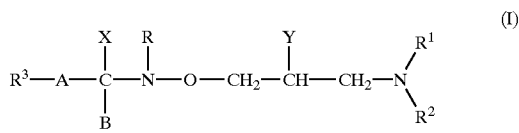

7 Claims, No Drawings

PHARMACEUTICAL COMPOSITION WITH ANTIVIRAL ACTIVITY CONTAINING AN HYDROXYMIC ACID DERIVATIVE AND AN ANTIVIRAL AGENT

This application is the national phase under 35 U.S.C. § 371 of PCT International Application No. PCT/IB98/00960 which has an International filing date of Jun. 22, 1998, which designated the United States of America. Which claim priority for Huagaum Patent Application No. P97 01 080 filed Jun. 23, 1997.

The invention relates to an antivirally pharmaceutical composition exerting an enhanced antiviral action and/or decreased side effect(s).

Antivirally active agents used e.g. for the treatment of HIV viral infections induce a general cellular injury in addition to the primary virus-injuring effect. Consequently, in a number of cases the chance of survival of the organism weakened also by the viral infection is hardly improved.

The hydroximic acid derivatives of formula (I)

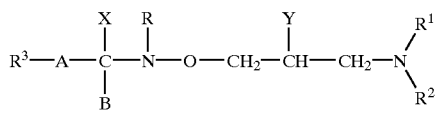

wherein $R^1$ means hydrogen or $C_{1-5}$alkyl group;

$R^2$ represents hydrogen; $C_{1-5}$alkyl group; $C_{3-8}$cycloalkyl group; or phenyl group optionally substituted by hydroxyl or phenyl group; or $R^1$ and $R^2$ together with the adjacent nitrogen atom form a 5 to 8 membered ring optionally containing additional nitrogen, oxygen or sulfur atom(s); and said ring can be condensed with an other alicyclic or heterocyclic ring, preferably with benzene, naphthalene, quinoline, isoquinoline, pyridine or pyrazoline ring; furthermore if desired and possible, nitrogen and/or sulfur as heteroatom(s) are present in the form of an oxide or dioxide;

$R^3$ stands for hydrogen or phenyl, naphthyl or pyridyl group optionally substituted by one or more halogen(s) or $C_{1-4}$alkoxy group(s);

Y means hydrogen; hydroxyl group; $C_{1-24}$alkoxy group optionally substituted by amino group; $C_{2-24}$polyalkenyloxy group containing 1 to 6 double bond(s);

$C_{1-25}$alkanoyl group; $C_{3-9}$ alkenoyl group; or a group of formula $R^7$—COO—, wherein $R^7$ is a $C_{2-30}$polyalkenyl group containing 1 to 6 double bond(s);

X represents halogen; amino group; or $C_{1-4}$alkoxy group;or

X and B together form an oxygen atom; or

X and Y together with the adjacent carbon atoms and the interjacent —NR—O—CH$_2$— group form a ring of formula (a),

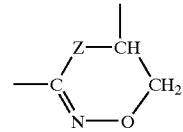

wherein
Z means oxygen or nitrogen;
R means hydrogen; or
R and B together represent a chemical bond;
A stands for $C_{1-4}$alkylene group or a chemical bond; or a group of the formula (b),

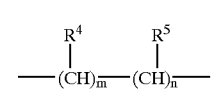

wherein
$R^4$ means hydrogen; $C_{1-5}$alkyl group; $C_{3-8}$cycloalkyl group; or a phenyl group preferably substituted by halogen, $C_{1-4}$alkoxy or $C_{1-5}$alkyl group;
$R^5$ means hydrogen; $C_{1-4}$alkyl group; or a phenyl group;
m is 0, 1 or 2; and
n is 0, 1 or 2, The U.S. Pat. No. 4,308,399 discloses compounds belonging to the scope of hydroximic acid derivatives of formula (I), which are useful for treatment of the diabetic angiopathy.

The EP-PS No. 417,210 describes hydroximic acid halides, which also fall into the scope of compounds of formula (I), possess a selective β-blocking effect and are useful for treatment of the diabetic angiopathy.

The Hungarian published patent application No. T/66350 discloses a number of other hydroximic acid derivatives being within the scope of compounds of formula (I). These known substances are useful in the therapy of vascular complications, particularly of diabetes mellitus.

It is known from the PCT Application No. WO/9713504 that hydroximic acid derivatives of formula (I) are useful for the prevention and treatment of disorders of mitochondrial origin. According to an investigation discussed in the description rats were treated with zidovudine (AZT), an antiviral nucleoside analogue useful in the therapy of AIDS, in order to correct the "defect" of the mitochondrial genom. This method resulted in animals suffering from hereditary cardiomyopathy. It was concluded from this investigation that the studied compounds of formula (I) diminished or prevented the mitochondrial membrane-injuring effect of zidovudine. However, it cannot be concluded from this establishment in any way that compounds of formula (I) were useful to diminish or to eliminate the unfavourable side effect of all known antivirally active substances.

The aim of the invention is to provide a pharmaceutical composition, which exerts an enhanced effect in comparison to that of the known antivirally active agent and/or decreases the side effects of the known antivirally active agent.

It has been found that the above aim can be achieved by the pharmaceutical composition according to the invention, which comprises a known antivirally active agent or, if desired and possible, a therapeutically useful acid addition salt thereof or therapeutically useful salt thereof, and a hydroximic acid derivative of formula (I), wherein R, $R^1$, $R^2$, $R^3$, A, B, X and Y are as defined above, or a therapeutically useful acid addition salt thereof together with one or more usual carrying materials.

Within the meanings of substituents defined in relation to the formula (I):

- $C_{1-5}$alkyl represents e.g. methyl, ethyl, n-propyl, isopropyl, n-butyl, or n-pentyl group, preferably methyl or ethyl group;
- $C_{3-8}$cycloalkyl stands e.g. for cyclopropyl, cyclopentyl, cyclohexyl, cycloheptyl or cyclooctyl group, preferably cyclonpentyl or cyclohexyl group;
- the 5 to 8 membered ring may be e.g. pyrrole, pyrazole, imidazole, oxazole, thiazole, pyridine, pyridazine, pyrimidine, piperazine, morpholine, indoline, quinoline ring or the like;
- the $C_{1-24}$alkoxy group may be e.g. methoxy, ethoxy, n-propoxy, tert-butoxy, n-pentoxy, decyloxy, dodecyloxy, octadecyloxy group or the like;
- the $C_{1-25}$alkanoyl group may represent e.g. formyl, acetyl, propionyl, butyryl, caproyl, palmitoyl or stearoyl group and the like;
- the $C_{3-9}$alkenoyl group means e.g. acryloyl, pentenoyl, hexenoyl, heptenoyl, octenoyl group or the like;
- the $C_{1-4}$alkylene group may be e.g. methylene, ethylene, propylene or butylene group;
- halogen may mean e.g. fluorine, chlorine, bromine or iodine, preferably chlorine or bromine. Y as $R^7$—COO— group may be e.g. linolenoyl, linoloyl, docosahexanoyl, eicosapentanoyl or arachidonoyl group or the like.

The physiologically (therapeutically) useful acid addition salts of the compounds of formula (I) are meant to be acid addition salts formed with therapeutically suitable inorganic acids, e.g. hydrochloric or sulfuric acid and the like; or with therapeutically useful organic acids, e.g. acetic, fumaric or lactic acid and the like.

Within the compounds of formula (I), a preferable subclass consists of hydroximic acid derivatives of formula (II), $$R^3-(CH)_m^{R^4}-(CH)_n^{R^5}-\underset{\underset{Y}{\parallel}}{C}-X \quad \underset{N-O-CH_2-CH-CH_2-N}{\overset{OH}{\phantom{|}}}\overset{R^1}{\underset{R^2}{\diagup}}$$  II wherein $R^1$, $R^2$, $R^3$, $R^4$, $R^5$, m and n are as defined for formula (I); X means halogen or amino group; and Y stands for hydroxyl group.

Compounds of formula (II), wherein $R^1$ and $R^2$ together with the adjacent nitrogen atom form a piperidino group, $R^3$ is a pyridinyl group, both m and n are 0, and X is as defined above, are particularly preferred. Of these 0-(3-piperidino-2-hydroxy-1-propyl)nicotinic acid amidoxime dihydrochloride (compound "L") is especially suitable.

An other advantageous subclass of the compounds of formula (I) consists of the compounds of formula (III), $$R^3-A-\overset{O}{\overset{\parallel}{C}}-NH-O-CH_2-\overset{OH}{\underset{\phantom{|}}{CH}}-CH_2-N\overset{R^1}{\underset{R^2}{\diagup}}$$  III wherein $R^1$, $R^2$, $R^3$ and A are as defined for formula (I).

A third preferred subclass of hydroximic acid derivatives of formula (I) includes cyclic compounds of formula (IV)

IV wherein $R^1$, $R^2$, $R^3$ and A are as defined for formula (I), and Z means oxygen or nitrogen.

A fourth preferred subclass of hydroximic acid derivatives of formula (I) comprises compounds of formula (V), $$R^3-A-\overset{OR^6}{\underset{\phantom{|}}{C}}=N-O-CH_2-\overset{OH}{\underset{\phantom{|}}{CH}}-CH_2-N\overset{R^1}{\underset{R^2}{\diagup}}$$  V wherein $R^1$, $R^2$, $R^3$ and A are as defined for formula (I) and $R^6$ stands for $C_{1-4}$alkyl group.

The compounds of formula (I) can be prepared by using processes known from U.S. Pat. No. 4,308,399 and EP-PS 417,210.

Known antivirally active agent (substance) is meant to be an antivirally active substance inhibiting the viral DNA polymerase, viral genom transcription, RNA polymerase, reverse transcriptase, helylase, primase, integrase, viral protein translation, the formation (developing) of viral regulating protein or viral structural protein and the like. The viral protease inhibitors are also included herein.

On the basis of chemical structure, the known antivirally active agents are chiefly purine and pyrimidine derivatives, nucleosides and nucleotides. Without limiting the possible known antivirally active agent of the pharmaceutical composition according to the invention to those listed below, preferred active agents of such type are e.g. as follows:

acyclovir: 9-[(2-hydroxyethoxy)methyl]-9H-guanine,
valacyclovir: L-valyl ester of acyclovir,
pencyclovir: 9-[4-hydroxy-3-(hydroxymethyl)-but-1-yl] guanine,
famcyclovir: diacetyl ester of pencyclovir,
gancyclovir: 9-(1,3-dihydroxy-2-propoxymethyl)guanine,
idoxuridine: 2'-deoxy-5-iodouridine,
floxuridine: 2'-deoxy-5-fluoruridine,
sorivudine: 1β-D-arabinofuranosyl-E-5-(2-bromovinyl) uracil,
trifluridine: 5-trifluoromethyl-2'-deoxyuridine,
vidarabine: 9β-D-ribofuranosyladenine,
zidovudine (AZT): 3'-azido-3'-deoxythymidine,
didanosine: 2',3'-dideoxyinosine,
zalcytabine: 2',3'-dideoxycytidine,
cytarabine: 4-amino-1-D-arabinofuranosyl-2(1H)-pyrimidinone,
dideoxyadenosine: 2',3'-dideoxyadenosine, and
edoxudine: 2'-deoxy-5-ethyluridine and the like.

The known antivirally active agent can be used also in the form of its therapeutically useful acid addition salt, if its chemical structure allows the preparation of an acid addition salt. Similarly;, the known antivirally active agent may be used as its therapeutically suitable salt, e.g. metal salt, ammonium salt or salts formed with organic bases, when its chemical structure is suitable for the preparation of such salts.

The pharmaceutical composition of the invention possessing an enhanced antiviral activity contains preferably zidovudine as antivirally active agent (ingredient); and 0-(3-piperidino-2-hydroxyl-1-propyl)-nicotinic acid amidoxime or a therapeutically useful acid, accition salt thereof as a hydroximic acid derivative of formula (I).

The pharmaceutical composition according to the invention commonly contains the active ingredients in amounts of 0.1 to 95% by weight, preferably 1 to 50% by weight, suitably 5 to 30% by weight together with the usual carrier (s) of pharmaceutical compositions.

In the pharmaceutical composition according to the invention, the weight ratio of the two active ingredients is preferably (1 to 50): (50 to 1), particularly preferably (1 to 10): (10 to 1).

The pharmaceutical composition of the invention can be a solid or liquid composition usefor for oral, parenteral or rectal administration or topical treatment.

The solid pharmaceutical compositions useful for oral administration can be powders, capsules, tablets, film-coated tablets, microcapsules and the like; and may contain as carrier(s) binders, e.g. gelatine, sorbitol, polyvinylpyrrolidine and the like; filling materials, e.g. lactose, glucose, starch, calcium phosphate and the like; tabletting aids such as magnesium stearate, talc, polyethylene glycol, silicon dioxide and the like; as well as wetting agents, e.g. sodium lauryl sulfate and the like.

The liquid pharmaceutical compositions for oral administration are solutions, suspensions or emulsions containing as carriers e.g. a suspending agent, such as gelatine, carboxymethylcellulose and the like; emulsifying agents, e.g. sorbitan monooleate; solvents such as water, oils, glycerol, propylene-glycol, ethanol; as well as preservatives such as methyl or propyl p-hydroxybenzoate and the like.

The pharmaceutical compositions for parenteral administration are usually the sterile solutions of the active agents (ingredients).

The dosage forms (dosage units) mentioned above as examples as well as other dosage forms are per se known, see e.g. the handbook: Remington's Pharmaceutical Sciences, Edition 18. Mack Publishing Co., Easton, USA (1990).

In the majority of cases, the pharmaceutical compositions according to the invention contain the dosage unit. For an adult person, the characteristic daily dose is 0.1 to 1000 mg of the known antivirally active agent and 0.1 to 1000 mg of a compound of formula (I), which can be administered once or in more subdoses. The actual dose depends on several factors and is determined by the physician.

The pharmaceutical compositions of the invention are prepared by admixing the active ingredient with one or more carrier(s), and converting the mixture obtained to a pharmaceutical composition in a manner known per se. Applicable methods are known from the literature, e.g., from the above mentioned Remington's Pharmaceutical Sciences manual.

The enhanced antiviral effect of the pharmaceutical composition of the invention was investigated by testing the inhibitory effect thereof on reverse transcriptase activity of Moloney murine virus(M-MuLV). Recombinant M-MuLV reverse transcriptase was purchased from New England Biolabs, USA. Measurement of the activity was carried out by investigating the poli(rA)$_n$oligo(dT)$_{12-18}$ template-primer directed incorporation of ($^3$H)dTTP(Amersham) into the cDNS.

In each case, the final volume of the reaction mixture was 20 microliters. The composition of the reaction mixture was as follows:
  2 microliters of 10× reverse transcriptase buffer,
  20 microgram/ml template primer,
  5 microM dTTP,
  2 microCi ($^3$H)dTTP, and
the test compound (dissolved in 1× reverse transcriptase buffer solution).

The composition of the 10× reverse transcriptase buffer (1 liter of solution contains the following substances):
  500 mM tris-hydrochloride/tris (hydroxy-methyl)-amino-methan-hydrochloride/(pH=8,3),
  80 mM magnesium-chloride
  300 mM potassium-chloride, and
  100 mM DTT (dithiotreitol).

The test materials were AZT and compound "L" added separately or together. The reaction was initiated by adding 5U reverse transcriptase. The reaction mixture was incubated for 40 min at 37° C. Then, 15 microliters of reaction mixture was transferred to Whatman DE81 filter-paper disc, washed by 5% by mass of aqueous disodium-hydrogenphosphate buffer, by water, and then with 96% by mass of ethanol. After drying, the discs were transferred into 5 ml of scintillation liquid (OptiPhase 'HiSafe 3', Wallac), and the radioactivity of samples was measured by a Packard Tri-Carb 2200 CE liquid scintillation counter. Enzymatic activity was calculated in percent from the experimental results. Experimental results are shown in Table 1.

TABLE 1

| Reverse transcriptase activity of Moloney murine leukemia virus | |
|---|---|
| Test compounds | Activity (%) |
| control | 100 |
| 0.1 microM/ml AZT | 91 |
| 0.2 microM/ml AZT | 84 |
| 0.02 mg/ml compound "L" | 75 |
| 0.03 mg/ml compound "L" | 74 |
| 0.1 microM/ml AZT + 0.02 mg/ml compound "L" | 67 |
| 0.2 microM/ml AZT + 0.02 mg/ml compound "L" | 55 |
| 0.2 microM/ml AZT + 0.03 mg/ml compound "L" | 57 |

Retroviruses, such as HIV or the murine leukemia virus used for the above experiment, are RNA viruses. They reproduce by synthesizing DNA with their reverse transcriptase, which then becomes integrated into the genom of the host cell. As shown in Table I., AZT by itself has only minor inhibitory effect on M-MuLV reverse transcriptase in the concentrations applied. In contrast, compound "L" has an inhibitory effect of about 25%. AZT and compound "L" decrease the enzyme activity to 55%, i.e., there is synergism between the two compounds.

Based on the above experimental results, it is concluded that the pharmaceutical compositions of the invention possesses an increased antiviral effect, therefore, it can be used for treating patients suffering from virus infection, during which the patient is treated with a known antiviral compound or its pharmaceutically acceptable acid addition salt supplemented by a hydroximic acid derivative of the formula I or a pharmaceutically acceptable acid addition salt thereof.

What is claimed is:

1. A method of treating a patient suffering from a viral infection comprising administering to the patient a pharmaceutically effective amount of a known antivirally active agent or a therapeutically useful acid addition salt or therapeutically useful salt of said known antiviral agent together with a pharmaceutically acceptable amount of a hydroximic acid compound of formula (I),

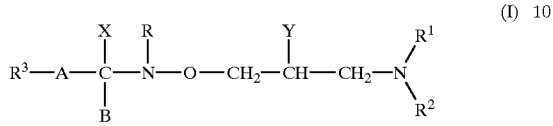

wherein

R$^1$ is a hydrogen or C$_{1-5}$alkyl group;

R$^2$ represents a hydrogen, C$_{1-5}$alkyl group, C$_{3-8}$cycloalkyl group or phenyl group optionally substituted by a hydroxyl or phenyl group;

R$^1$ and R$^2$ together with the adjacent nitrogen atom form a 5 to 8 membered ring optionally containing additional nitrogen, oxygen or sulfur atom(s), and said ring can be condensed with a alicyclic or heterocyclic ring, and nitrogen and/or sulfur as heteroatom(s) are optionally present in the form of an oxide or dioxide;

R$^3$ represents a hydrogen or phenyl, naphthyl or a pyridyl group optionally substituted by one or more halogen(s) or C$_{1-4}$alkoxy group(s);

Y represents a hydrogen, hydroxyl group, C$_{1-24}$alkoxy group optionally substituted by an amino group, C$_{1-24}$polyalkenyloxy group containing 1 to 6 double bond(s), C$_{1-25}$alkanoyl group, C$_{3-9}$alkenoyl group, or a group of formula R$^7$—COO— wherein R$^7$ is a C$_{2-30}$polyalkenyl group containing 1 to 6 double bond(s);

X represents a halogen, amino group, or C$_{1-4}$alkoxy group; or

X and B together represent an oxygen atom; or

X and Y together with the adjacent carbon atoms and the interjacent —NR—O—CH$_2$— group form a ring of formula (a),

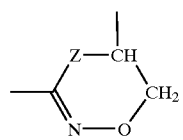

wherein Z represents an oxygen or nitrogen;

R represents a hydrogen; or

R and a together form a chemical bond;

A represents a C$_{1-4}$alkylene group, a chemical bond, or a group of the formula (b),

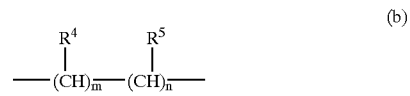

wherein

R$^4$ represents a hydrogen, C$_{1-5}$alkyl group, C$_{3-8}$cycloalkyl group, or phenyl group optionally substituted by halogen, C$_{1-4}$alkoxy, or C$_{1-5}$alkyl group;

R$^5$ represents a hydrogen, C$_{1-4}$alkyl group, or phenyl group;

m is 0, 1, or 2; and n is 0, 1, or 2;

or a therapeutically useful acid addition salt thereof.

2. The method according to claim 1, which comprises using zidovudine as the known antiviral agent; and 0-(3-piperidino-2-hydroxyl-1-propyl)nicotinic acid amid-oxime or a therapeutically useful acid addition salt thereof as a hydroximic acid compound.

3. A method of treating a patient with HIV comprising administering a pharmaceutically effective amount of the compound of Formula I or pharmaceutically acceptable salts thereof as defined in claim 1 along with a pharmaceutically acceptable carrier, binder, filler, vehicle, diluent, or excipient or any combination thereof.

4. A method of treating a patient with murine leukemia comprising administering a pharmaceutically effective amount of the compound of Formula I or pharmaceutically acceptable salts thereof as defined in claim 1 along with a pharmaceutically acceptable carrier, binder, filler, vehicle, diluent, or excipient or any combination thereof.

5. The method of claim 3, comprising administering a pharmaceutically effective amount of the compound of Formula I with a compound selected from the group consisting of zidovudine, 0-(3-piperidino-2-hydroxyl-1-propyl) nicotinic acid amid-oxime, and pharmaceutically acceptable salts of zidovudine, 0-(3-piperidino-2-hydroxyl-1-propyl) nicotinic acid amid-oxime.

6. The method of claim 4, comprising administering a pharmaceutically effective amount of the compound of Formula I with a compound selected from the group consisting of zidovudine, 0-(3-piperidino-2-hydroxyl-1-propyl) nicotinic acid amid-oxime, and pharmaceutically acceptable salts of zidovudine, 0-(3-piperidino-2-hydroxyl-1-propyl) nicotinic acid amid-oxime.

7. The method of claim 1, wherein said alicyclic or heterocyclic ring is a benzene, naphthalene, quinoline, isoquinoline, pyridine or pyrazoline ring.

* * * * *